(12) United States Patent
Trautwein et al.

(10) Patent No.: US 10,117,680 B2
(45) Date of Patent: Nov. 6, 2018

(54) OSTEOSYNTHESIS DEVICE

(71) Applicant: Silony Medical International AG, Frauenfeld (CH)

(72) Inventors: Frank Thilo Trautwein, Filderstadt (DE); Frank Heuer, Filderstadt (DE); Timo Ohnmacht, Trichtingen (DE)

(73) Assignee: Silony Medical International AG, Frauenfeld (CH)

( * ) Notice: Subject to any disclaimer, the term of this patent is extended or adjusted under 35 U.S.C. 154(b) by 0 days.

(21) Appl. No.: 15/500,981

(22) PCT Filed: Jul. 15, 2015

(86) PCT No.: PCT/EP2015/066148
§ 371 (c)(1),
(2) Date: Feb. 1, 2017

(87) PCT Pub. No.: WO2016/020158
PCT Pub. Date: Feb. 11, 2016

(65) Prior Publication Data
US 2017/0209185 A1 Jul. 27, 2017

(30) Foreign Application Priority Data

Aug. 6, 2014 (DE) .................. 10 2014 215 529

(51) Int. Cl.
*A61B 17/70* (2006.01)
(52) U.S. Cl.
CPC ...... *A61B 17/7037* (2013.01); *A61B 17/7032* (2013.01)
(58) Field of Classification Search
CPC ..................... A61B 17/70–17/7046
See application file for complete search history.

(56) References Cited

U.S. PATENT DOCUMENTS

| 5,873,878 A | 2/1999 | Harms et al. |
| 7,211,086 B2 | 5/2007 | Biedermann et al. |

(Continued)

FOREIGN PATENT DOCUMENTS

| DE | 602005002477 T2 | 1/2008 |
| DE | 102007042953 | 3/2009 |
| DE | 102011001016 | 9/2012 |

OTHER PUBLICATIONS

International Search Report and Written Opinion from PCT/EP2015/066148 dated Oct. 20, 2015.

*Primary Examiner* — Nicholas Plionis
(74) *Attorney, Agent, or Firm* — Dilworth & Barrese, LLP

(57) ABSTRACT

The invention relates to an osteosynthesis device having a bone screw (12), which has a threaded shaft (24) and a ball head (26), and having a fork head (14), which has a groove (32) and two legs (34), the ball head (26) being pivotably supported in the fork head (14), and having a pressure piece (16), which is seated on the ball head (26), the pressure piece (16) being braced on the fork head (14) and having two lateral fins (48) extending in the axial direction (30) of the fork head (14) and away from the threaded shaft (24); it is proposed that the pressure piece (16) is supported in the fork head (14) with prestressing in the axial direction (30) and thus in the direction toward the ball head (26) in that at least one of the fins (48) is slit transversely to the axial direction (30) of the fork head (14), so that a slit (50) forms a spring tongue (52), and the pressure piece (16) is thereby resiliently embodied and is braced via the spring tongue (52) on the fork head (14), and that a protrusion (70) protrudes in the axial direction (30) into the slit (50); and that the protrusion (70), for limiting deformation or deflection of the spring tongue (52), forms a stop (72), acting in the axial direction (30), for the spring tongue (52).

17 Claims, 11 Drawing Sheets

(56) References Cited

U.S. PATENT DOCUMENTS

Figures 1A, 1B:
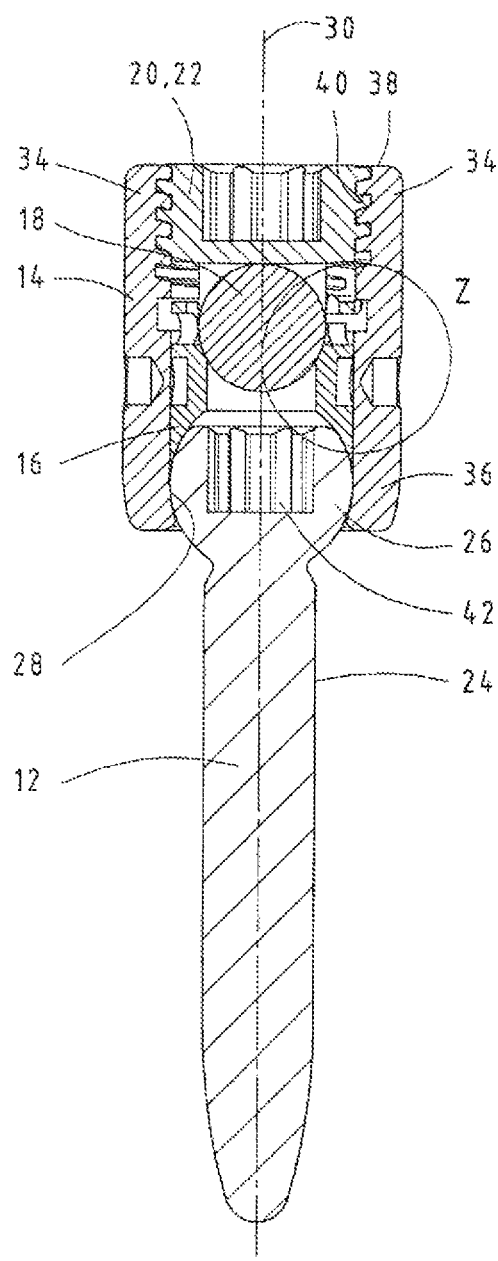

| | | |
|---|---|---|
| 7,955,359 B2 | 6/2011 | Matthis et al. |
| 8,562,652 B2 | 10/2013 | Biedermann et al. |
| 2006/0241599 A1 | 10/2006 | Konieczynski et al. |
| 2010/0137920 A1 | 6/2010 | Hammill et al. |
| 2011/0046683 A1 | 2/2011 | Biedermann et al. |
| 2011/0077694 A1 | 3/2011 | Biedermann et al. |
| 2011/0160778 A1 | 6/2011 | Elsbury |
| 2011/0282399 A1 | 11/2011 | Jackson |
| 2012/0046699 A1 | 2/2012 | Jones et al. |
| 2012/0209336 A1* | 8/2012 | Jackson ............ A61B 17/7032 606/305 |
| 2012/0310284 A1 | 12/2012 | Gerchow |
| 2015/0196338 A1* | 7/2015 | Biedermann ...... A61B 17/7037 606/305 |

* cited by examiner

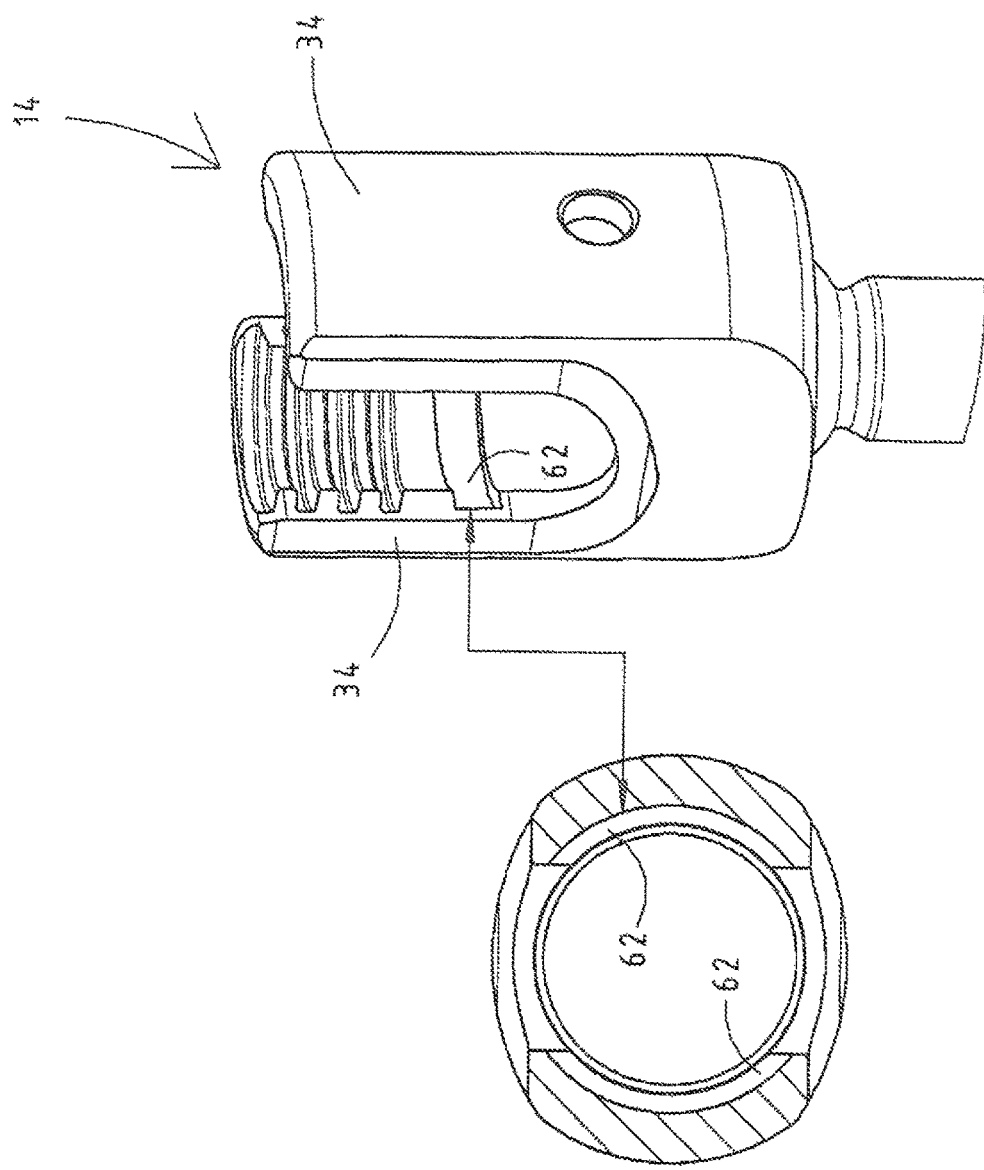

OSTEOSYNTHESIS DEVICE

This application claims priority to International Application No. PCT/EP2015/066148, filed on Jul. 15, 2015, which claims priority to German Patent Application No. 102014215529.0, filed on Aug. 6, 2014.

The invention relates to an osteosynthesis device having a bone screw which has a threaded shaft and a ball head, and having a fork head which has a groove and two legs, the ball head being pivotably supported in the fork head, and having a pressure piece which is seated on the ball head, the pressure piece being braced on the fork head and having two lateral fins extending in the axial direction of the fork head and away from the threaded shaft, for instance for a connecting rod to be placed in the groove of the fork head between the two legs. The term "ball head" is also understood to be a screw head that has a bearing face that is not embodied exactly spherically, as long as it cooperates with the fork head in the manner of a spherical cap bearing.

A generic osteosynthesis device is known for instance from US 2006/0241599 A1.

From DE 196 17 362 C2, an anchoring element is known, which has a bone screw with a shaft and a fork head; a connecting rod is placed in the fork head and fixed. An insert element is also provided, which forms a support for the connecting rod.

EP 1 323 391 A2 shows a polyaxial screw with a threaded shaft and a spherical-segmental head that is supported in a fork head. A pressure piece is seated on this ball head and also forms a support for the connecting rod. The pressure piece is pressed against the ball head by a screw sheath screwed into the fork head.

From WO 2004/098423 A1, a polyaxial screw is known in which the ball head of the bone screw, located in the fork head, is pressed by the connecting rod elastically into the spherical cap receiving it. Without the connecting rod, the connecting element does not exert any forces on the ball head.

From US 2006/0241599 A1, a polyaxial screw is known in which a pressure piece has slits, extending in the longitudinal direction, so that a wall area between them of the pressure piece, as a result of a radially inward-oriented deformation of the fork head, is likewise deflectable radially inward and in the process exerts a clamping force on the ball head of the bone screw.

From US 2010/0137920 A1, a polyaxial screw is known in which a pressure piece is subjected to force in the longitudinal direction against the ball head of the bone screw via helical springs.

Further osteosynthesis devices are known from DE 60 2005 002 477 T2 and US 2011/0077694 A1.

The object of the invention is to further refine an osteosynthesis device of the type defined at the outset in such a way that it is more conveniently manipulatable in the surgical implantation.

This object is attained, in an osteosynthesis device of the type defined at the outset, in a first variant of the invention (claim 1) in that the pressure piece is supported in the fork head with prestressing in the axial direction and thus in the direction toward the ball head, in that at least one of the fins is slit transversely to the axial direction of the fork head, so that a slit forms a spring tongue, and the pressure piece is thereby resiliently embodied and is braced via the spring tongue on the fork head; and that a protrusion protrudes in the axial direction into the slit; and that the protrusion, for limiting deformation or deflection of the spring tongue, forms a stop, acting in the axial direction, for the spring tongue.

The pressure piece is accordingly braced on the one hand against the fork head in the axial direction and on the other, as a consequence of its resilient embodiment, it presses against the ball head of the bone screw. Since under axial prestressing the pressure piece is braced on the one hand on the fork head and on the other on the ball head of the bone screw, no connecting rod or other means is required for fixing the fork head beforehand relative to the ball head and the threaded shaft in such a way as to prevent unwanted swiveling of the fork head relative to the ball head, or at least making it more difficult. As a result of the axial prestressing of the pressure piece, the ball head of the bone screw is accordingly placed relative to a spherical cap-like bearing face on the fork head in a maximally nondisplaceable way. This can already be helpful when the bone screw is being screwed in.

By itself, the correct seat of the pressure piece on the fork head already assures the nonpositive engagement between the bone screw and the pressure piece and thus a fixation beforehand between the bone screw mid the fork head by means of the pressure piece. The fork head and the bone screw can accordingly be adjusted relative to one another in a desired manner or orientation, and they maintain this orientation, which significantly facilitates the surgery for implanting and completing the entire osteosynthesis device.

The pressure piece has two lateral fins, extending in the axial direction of the fork head and away from the threaded shaft. These fins, when the pressure piece is inserted into the fork head, extend in particular parallel to the legs of the fork head. One of the tasks of the fins is to brace the pressure piece on the fork head, so that forces can be transmitted between the pressure piece and the fork head. In the process, forces in the axial direction of the fork head are intended to be transmitted to the ball head of the bone screw, which is supported in the spherical cap-like bearing face of the fork head.

The osteosynthesis device of the invention has the substantial advantage on the one hand that the bone screw with its ball head is supported in the fork head by nonpositive engagement, so that the fork head can be oriented relative to the ball head by the surgeon before being screwed in or only after being screwed into the bone. Then, it cannot tilt out of the way laterally, so that all the fork heads can be aligned and remain aligned, so that a connecting rod or correction rod can in a certain sense be placed simultaneously in the fork heads. The osteosynthesis device of the invention thus makes implanting the osteosynthesis device much easier, and implantation can furthermore be done faster.

According to the invention, because of both the slit-type embodiment of at least one fin of the pressure piece and the intrinsic embodiment of a spring tongue, it is attained that the aforementioned prestressing acting in the axial direction can be implemented directly by means of slight axial compression of the pressure piece. Thus according to the invention, inside the pressure piece, that is, inside at least one fin of the pressure piece, an axial elastic resilience, that is, acting in the axial direction of the fork head, is achieved, so that when the pressure piece is being clipped or latched or twisted into place into an installed position on the fork head, an axial prestressing in the axial direction of the fork head and thus in the direction toward the ball head is attained.

It is furthermore proposed according to the invention that the deformation or deflection of the spring tongue, as the pressure piece is clipped or latched or screwed into its installed position is limited, specifically by means of a protrusion protruding into the slit in the axial direction; the protrusion here forms a stop for the spring tongue. In this way it can be prevented according to the invention that in the spring tongue, in particular in the vicinity of the articulated connection of the spring tongue to the fixed part of the pressure piece, overly strong forces in the course of the deflection of the spring tongue will occur which could cause plastic deformation of the pressure piece, which could prove disadvantageous.

The aforementioned protrusion protruding into the slit can, in one embodiment of the invention, be embodied opposite the spring tongue on the pressure piece and in particular can be embodied there in one piece with the pressure piece. In a further embodiment of the invention, it can also be embodied on the spring tongue, in particular being embodied in one piece with the spring tongue.

It further proves advantageous if the protrusion is embodied, on a free end of the spring tongue or on an area of the pressure piece opposite the free end of the spring tongue in the axial direction. In such a case, when the protrusion is in place an oblong-slotlike opening is formed between the spring tongue and the remaining part of the pressure piece.

Figure 3A:
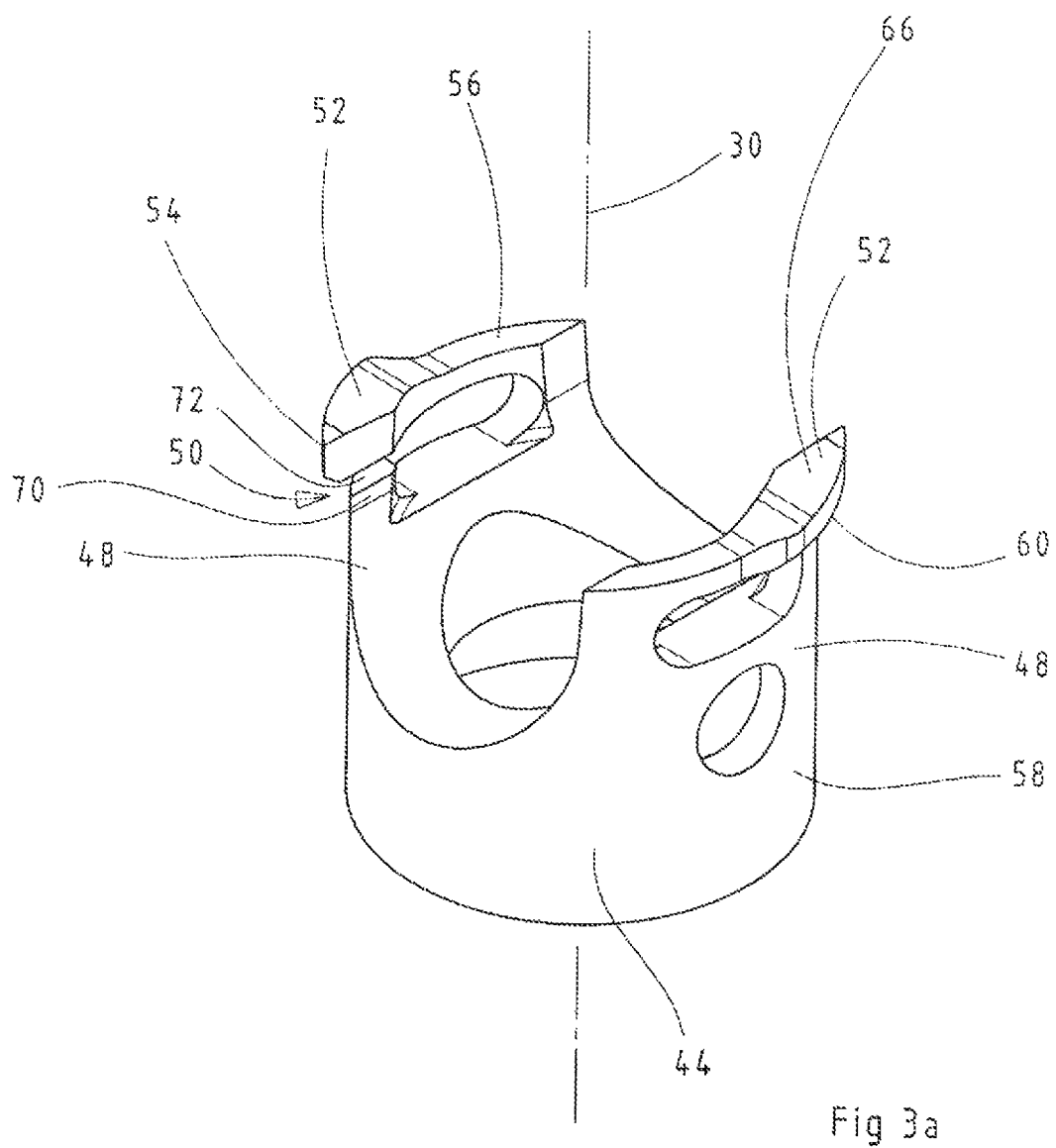

As mentioned above, the pressure piece can be embodied as slit-type on one or both fins. In the latter case, which is considered preferable, it may prove advantageous if the pressure piece and its fin are embodied as axially symmetrical, or in other words rotationally symmetrical, to the axial direction of the fork head. Such an embodiment is shown in FIG. 3a.

Figure 3B:
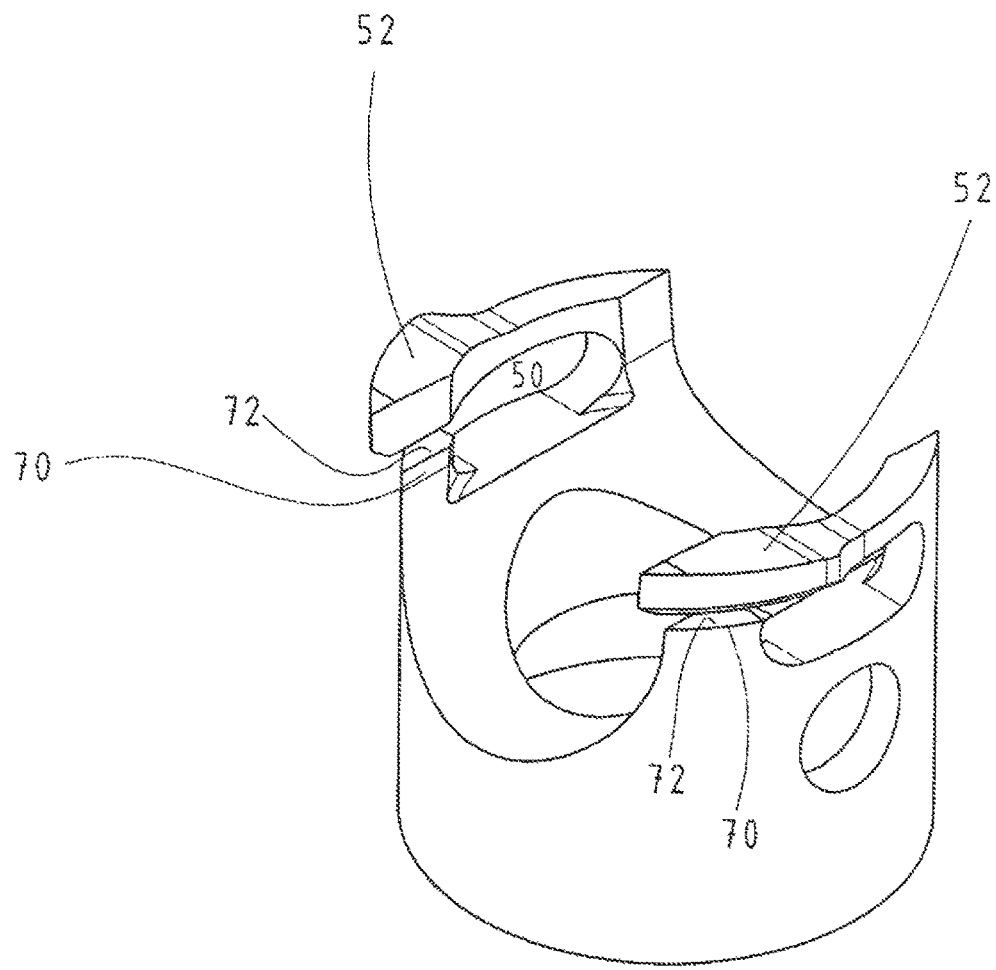

It can also prove advantageous if the pressure piece and its fin are embodied as mirror-symmetrical to a plane that includes the axial direction of the fork head. Such an embodiment is shown in FIG. 3b.

Figure 4A:
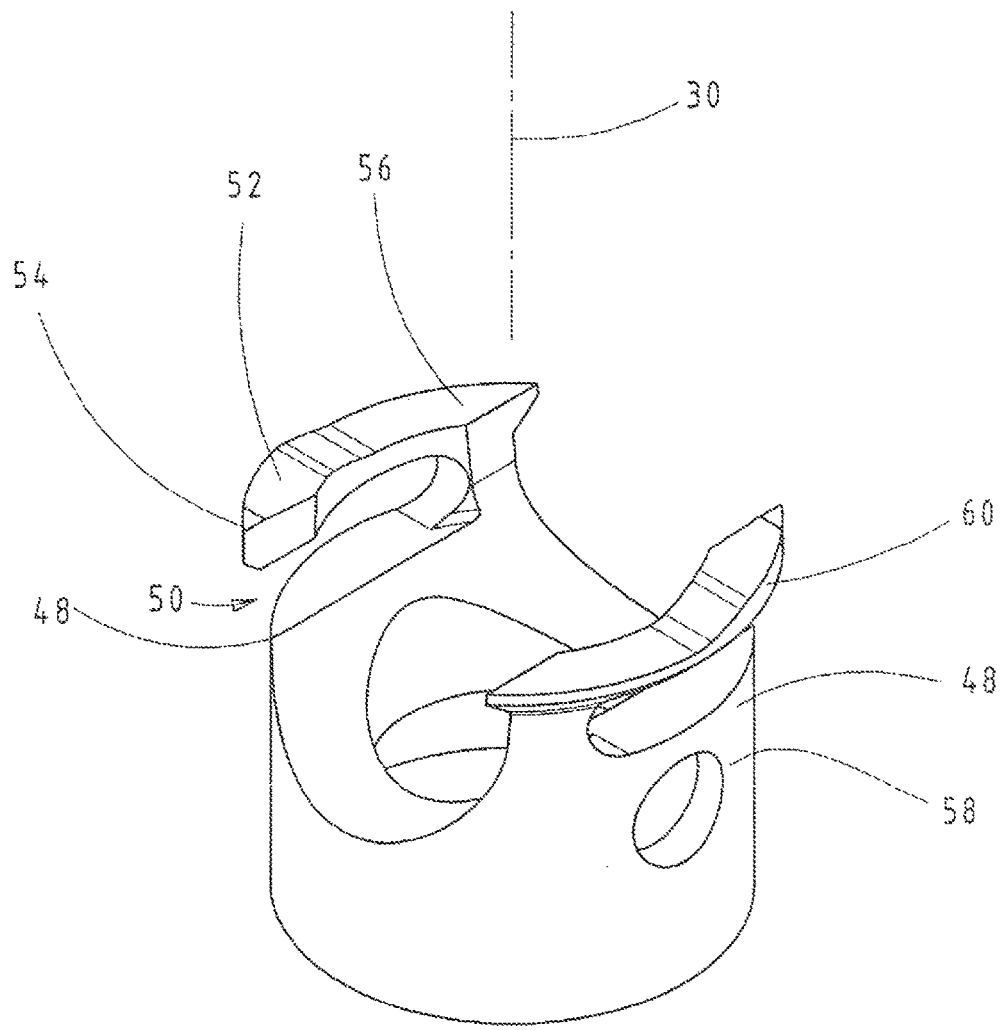
Figure 4B:
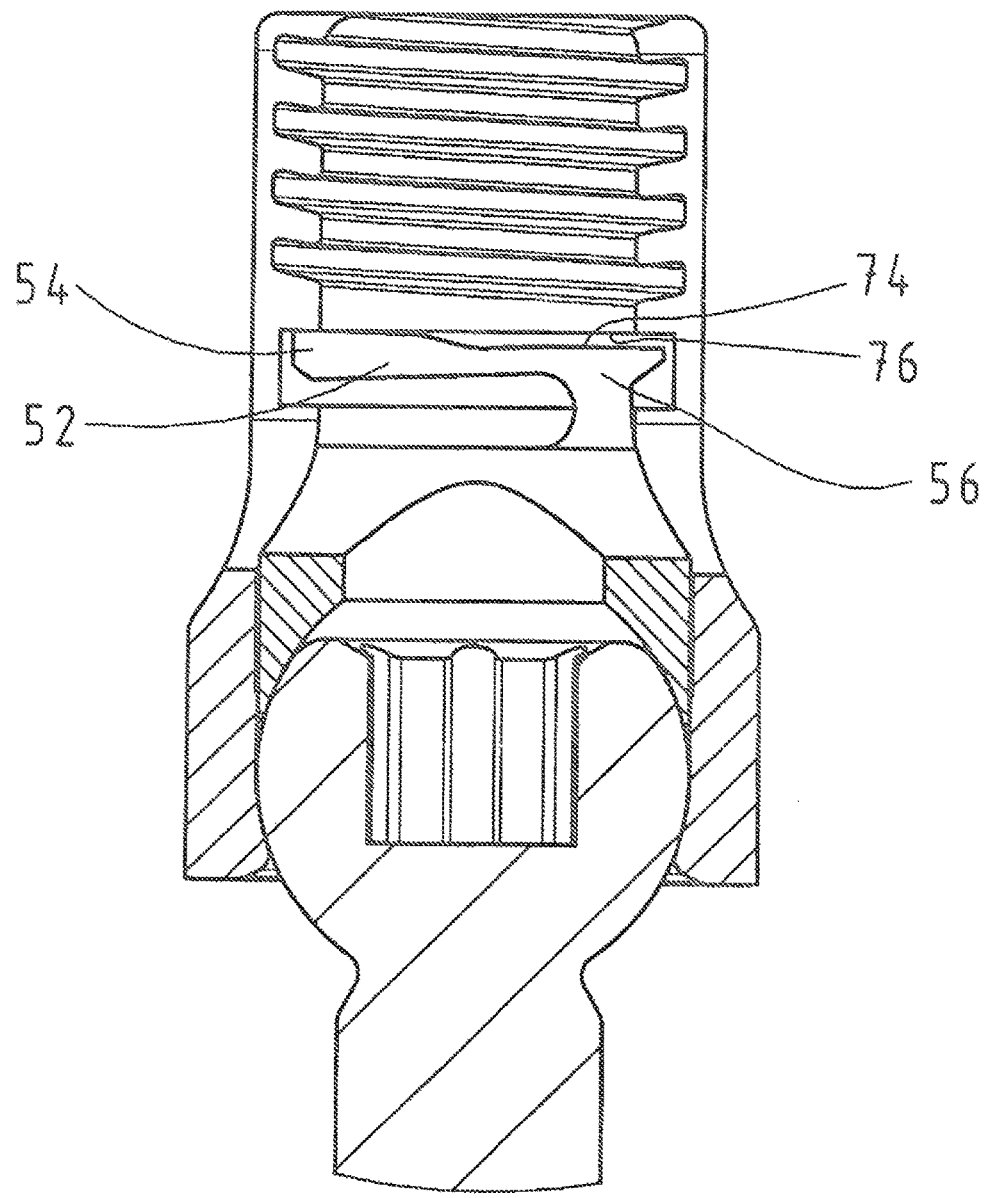
Figure 4C:
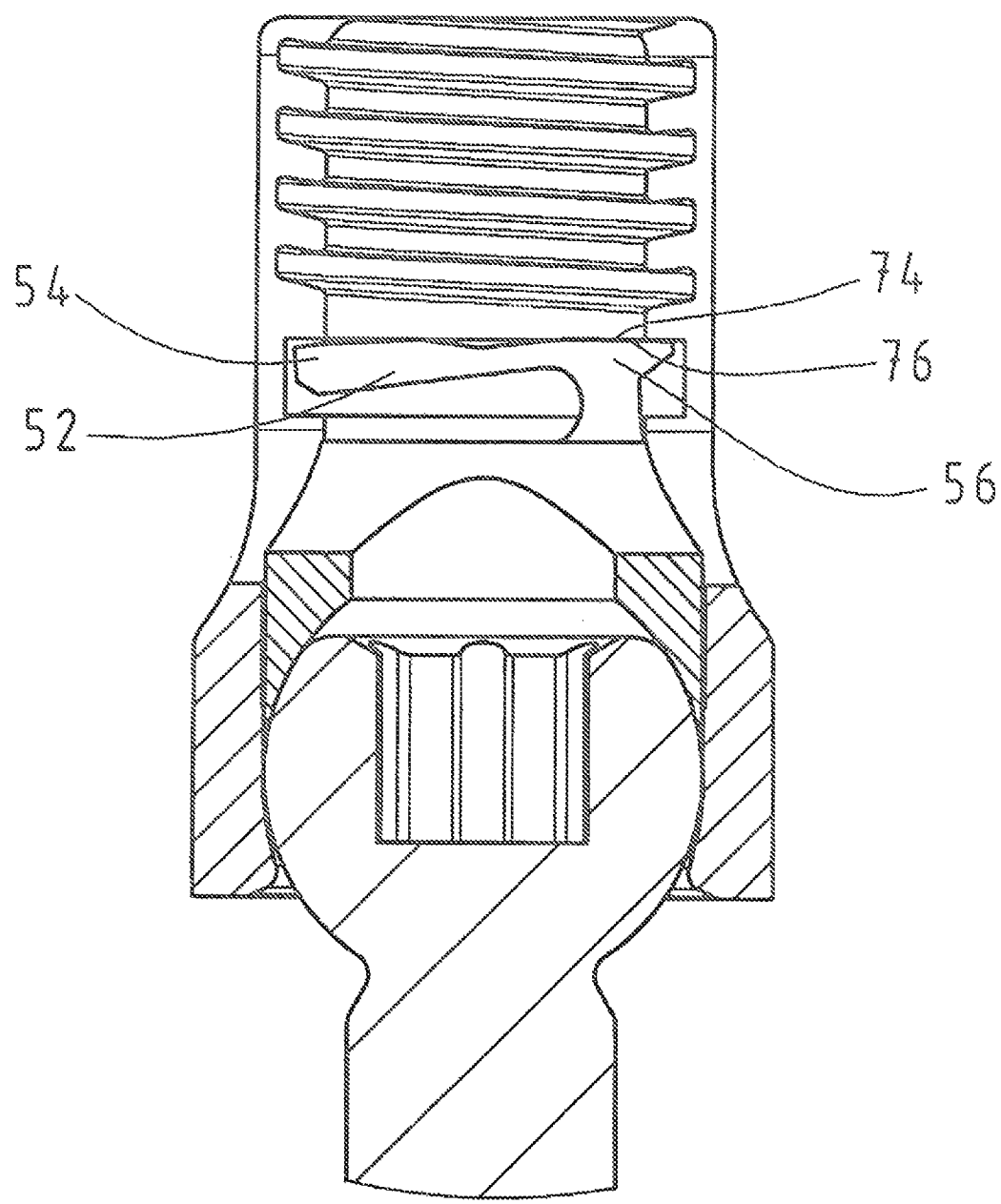

The above object is attained in a second variant of the invention (claim 5) in that the pressure piece is supported in the fork head with prestressing in the axial direction and thus in the direction toward the ball head in that at least one of the fins is slit transversely to the axial direction of the fork head, so that a slit forms a spring tongue, and the pressure piece is thereby resiliency embodied and is braced via the spring tongue on the fork head; and that the spring tongue, in the state in which it is installed on the fork head but is not additionally axially stressed, is spaced apart in the vicinity of its end, joined to the fin, from the fork head in the axial direction; and that the spring tongue, in the additionally axially stressed slate, in the vicinity of its end joined to the fin forms a stop and can be braced with the stop against the fork head for limiting more-extensive deformation or deflection of the spring tongue. This variant of the invention is shown in FIGS. 4a-c. In both variants, an overly extensive deformation of the spring tongue is prevented by embodying a stop that limits the deflection of the spring tongue.

In the state in which it is installed on the fork head but not additionally axially stressed, the spring tongue is preferably braced, in the vicinity of its free end, against the fork head.

In both variants of the invention, it further proves advantageous if the slit, on its closed end, or in other words where the spring tongue changes over into the remaining part of the pressure piece, is embodied in rounded fashion. On the other, open end, it can also prove advantageous if the protrusion provided there changes over in rounded fashion into the spring tongue or into the fixed part of the pressure piece.

It is further proved advantageous if the deflection of the spring tongue, upon the clasping or latching or screwing in of the pressure piece into its installed position in the fork head, amounts to at most 1.0 mm, in particular at most 0.5 mm, and more particularly at least 0.1 mm. In this way, overly strong tensions inside the pressure piece, which could lead to plastic deformations of the pressure piece, are securely prevented from happening.

In view of simple, safe and secure operation of the pressure piece and its expedient installation on the fork head in a way that is expedient for the surgeon to do, it proves advantageous if on outer sides of the fins of the pressure piece, there are protrusions or recesses, which cooperate in intermeshing fashion with recesses or protrusions on inside surfaces of the legs of the fork head, or in other words thus keeps the pressure piece axially prestressed on the fork head, so that it presses on the ball head and thus pre-fixes the fork head in by nonpositive engagement relative to the ball head and relative to the threaded shaft.

For thus purpose, in an embodiment of the invention, it is proposed that the pressure piece engages a graduation step, located on an inner side of a leg of the fork head, from beneath or engages the inside of a recess embodied there. For this purpose, particularly on its end remote from the ball head, the pressure piece can have a radially protruding edge, or even only one or a plurality of radially protruding extensions, which can then be clipped or latched or screwed into this graduation or recess on the fork head such that, when the pressure piece is put in its installed position on the fork head, the spring tongue formed by the slit is deflected slightly. Preferably, the pressure piece is introduced into the fork head in the axial direction of the fork head and then screwed into its installed position about the axial direction.

It can furthermore be advantageous that one fin or both fins of the pressure piece are embodied with multiple slits, or in other words have a plurality of slits, which are cut inward into the fin or fins in alternation from one side and a side opposite that side transversely to the axial direction of the fork head. Thus correspondingly a plurality of spring tongues are formed.

The pressure piece of the osteosynthesis device of the invention can directly or indirectly form a support for the connecting rod. After the fixation of the connecting rod by tightening an additional fixation means, in particular a grub screw, into a thread on the free end of the fork bead, the connecting rod, via the pressure piece, presses on the ball head and the bearing face of the fork head, so that all the components, at the end of the operation are permanently tensed and fixed to one another. The axial prestressing embodied beforehand in the pressure piece then has practically no further function.

In a further concept of the invention, it proves advantageous if the pressure piece is secured against relative rotation with respect to the fork head, or in other words is not rotatable about the axial direction of the fork head. This can be implemented for instance by means of a longitudinal or sliding fit guide extending parallel to the axial direction, or in some other way.

An embodiment also proves advantageous in which the spring tongue is embodied as thicker on the free end (54) in the radial and/or axial direction than at the closed end.

Separately from the inventive definition, described above, of the deflection of the spring tongue by means of a protrusion protruding into the slit, independent protection is claimed for an osteosynthesis device having a bone screw which has a threaded shaft and a ball head, and having a fork head which has a groove and two legs, the ball head being pivotably supported in the fork head, and having a pressure piece which is seated on the ball head, the pressure piece being braced on the fork head and having two lateral fins extending in the axial direction of the fork head and away from the threaded shaft, and the osteosynthesis device is characterized in that the pressure piece is supported in the fork head with prestressing in the axial direction and thus in the direction toward the ball head in that at least one of the fins is slit transversely to the axial direction of the fork head, so that a slit forms a spring tongue, and the pressure piece is thereby resiliently embodied and is braced via the spring tongue on the fork head; and that the spring tongue, in the state in which it is installed on the fork head but is not additionally axially stressed, is spaced apart in the vicinity of its end, joined to the fin, from the fork head in the axial direction; and that the spring tongue, in the additionally axially stressed state, in the vicinity of its end joined to the fin forms a stop and can be braced with the stop against the fork head for limiting more-extensive deformation or deflection of the spring tongue. Thus on the one hand the pressure piece is braced against the fork head in the axial direction and on the other, as a consequence of its resilient embodiment, it presses on the ball head of the bone screw.

Further features, details and advantages of the invention will become apparent from the appended patent claims and the drawings and the ensuing description of preferred embodiments of the invention. The features shown in the drawings and mentioned in the claims and in the specification can each be inventive, either individually, or in arbitrary combination.

IN THE DRAWINGS

Figure 2B:
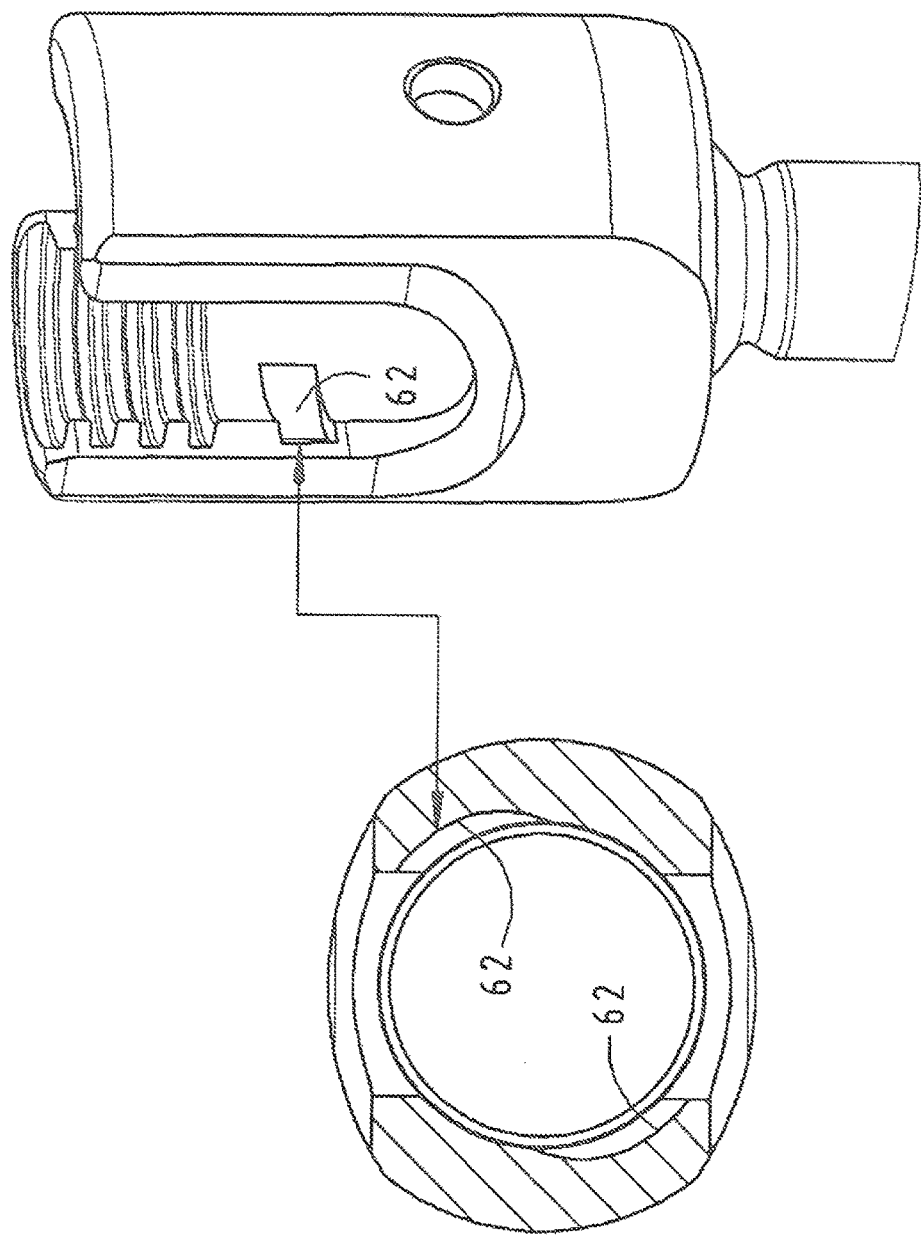
Figure 2C:
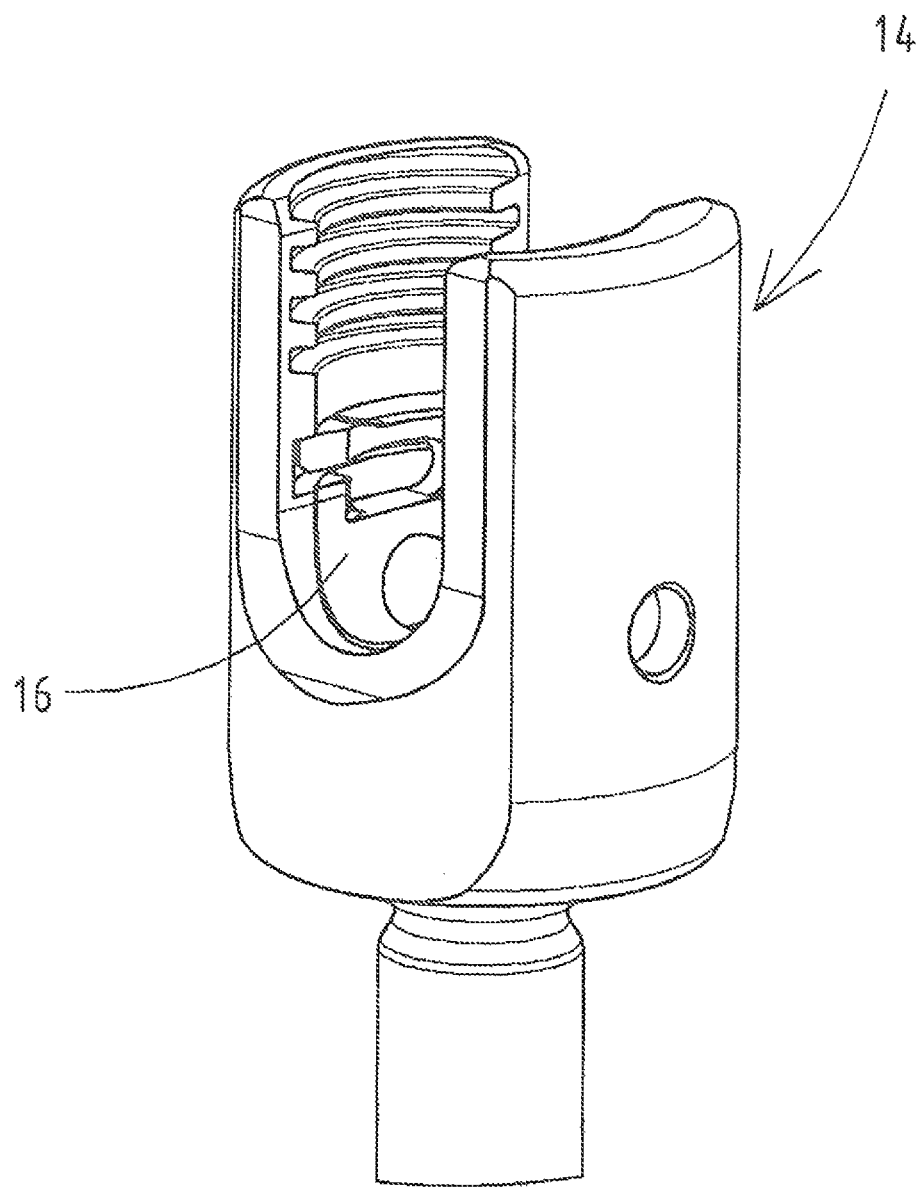
Figure 3C:
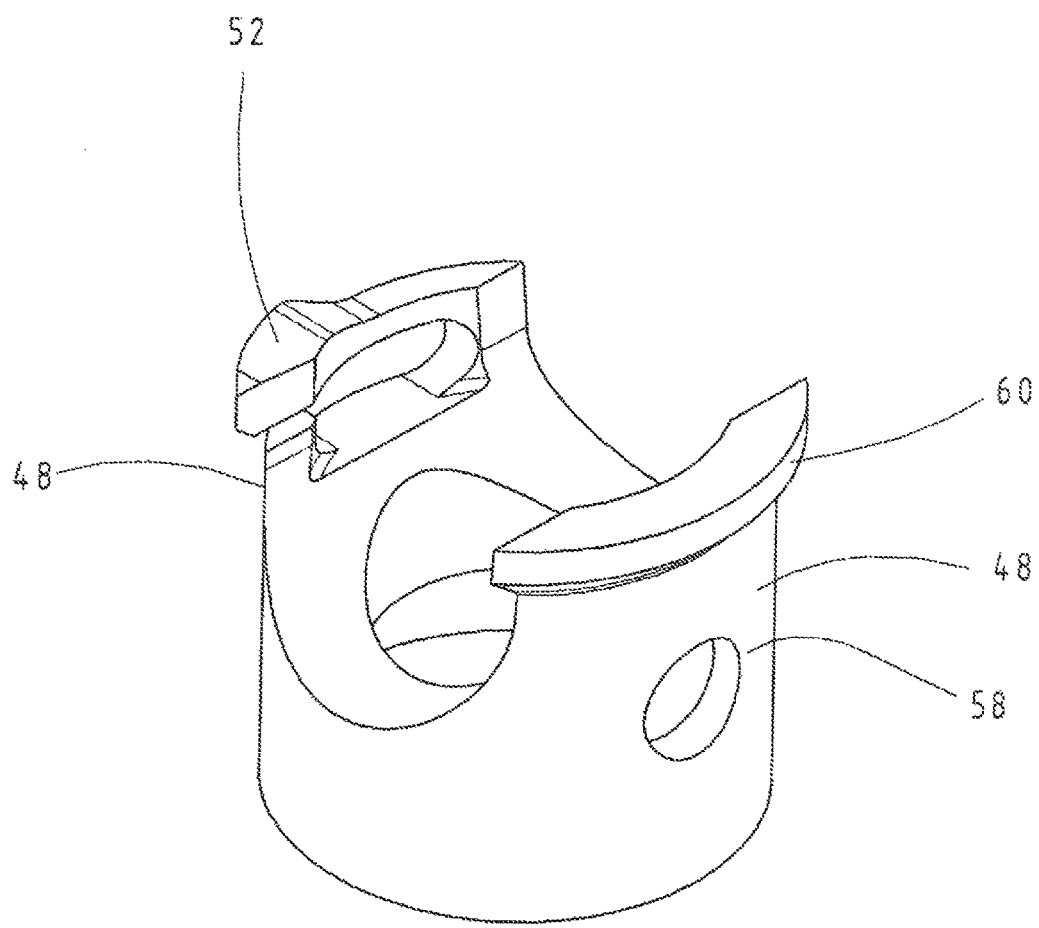

FIGS. 1a, b show an osteosynthesis device of the invention, identified by reference numeral 10, and a detailed view;

FIGS. 2a, b show fragmentary views of a fork head with a bone screw for the osteosynthesis device of the invention in perspective and in section;

FIGS. 2c, d show fragmentary perspective views of the fork head with the bone screw of FIG. 2a with the pressure piece inserted;

FIGS. 3a-c show perspective views of three embodiments of a pressure piece of the osteosynthesis device of the invention, in a first variant of the invention;

FIGS. 4a-c show a farther embodiment of the osteosynthesis device of the invention, in a second variant of the invention, both in perspective and in fragmentary sectional views.

The osteosynthesis device includes a bone screw 12, a fork head 14, a pressure piece 16, a sketchily shown correction, supporting or connecting means or rod 18, and a clamping means 20 that is embodied for example in the form of a grub screw 22. In the invention being discussed here, the cooperation of the pressure piece 16 with the fork head 14 and the bone screw 12 is crucial. The bone screw 12 has a threaded shaft 24 as well as a ball head 26, which in the case shown merely as an example are embodied in one piece, but can also be formed by two parts joined to one another. The ball head 26 is received in articulated or pivotable fashion in a spherical cap 28 of the fork bead 14 and can be positioned relative to it, in a manner to be described hereinafter, nonpivotably by nonpositive engagement.

The fork head 14, which is also shown in perspective in FIGS. 2a and 2b, is embodied approximately cylindrically or in cuplike fashion; the cylinder or cup shape is interrupted in such a way that a groove 32, extending transversely to the axial direction 30, is formed for inserting the correcting, supporting or connecting means 18. This groove 32 is bounded in the circumferential direction by two legs 34, which extend in the axial direction 30 and are embodied concentrically, diametrically opposite one another in the axial direction 30. The legs 34 are connected toward the bottom, that is, in the direction of the ball head 26, by a circumferentially closed and in particular ringlike or cylindrical base region 36 and are preferably embodied in one piece with it. The legs 34, beginning at their tree end 38, have a female thread 40, into which the grub screw 22 can be screwed. Before the grab screw 22 is screwed into the fork head 14 in order to clamp the correcting, supporting or connecting means 18, however, the bone screw 12 must first be screwed into the bone. For this purpose, the surgeon reaches from above with a suitable tool down between the legs 34 of the fork head 14 and places the tool, not shown, in or on a tool engagement location 42 embodied on the ball bead 26. In order during this procedure to keep the fork head 14 in a suitable position and essentially to keep it rigidly on the ball head 26, the pressure piece 16 is employed. The pressure piece 16, shown in mounting position in FIG. 1a, is shown in perspective in FIG. 3a. The pressure piece 16, toward the ball head 26, includes a pressure ring 44 with a sliding face 46 (see FIG. 1b) that faces toward the ball head 26 and can be placed against it in the manner of a spherical cap bearing. Two fins 48 originating at the pressure ring 44 extend on diametrically opposed sides relative to the axial direction 30. At least one of the fins 48 is embodied as slit extending transversely to the axial direction 30. In this way, a slit 50 thereby formed forms a spring tongue 52. The spring tongue 52 is accordingly a part of the applicable fin 48 and is bounded by the slit-type embodiment of this fin 48 transversely to the axial direction 30 and thereby formed. The spring tongue 32 includes one free end 54 and one end 56 with which it remains joined to the remainder of the respective fin 48. The spring tongue 52 can be deflected axially, that is, in the axial direction 30, so that the respective fin 48 and as a result the pressure piece 16 as a whole can be put under prestressing in the axial direction 30. By means of this prestressing, the pressure piece 16 can be braced on the one hand against the fork head 14 in a manner to be described hereinafter and on the other against the ball head 26. In this way, the ball head and thus the threaded shaft 24 can be placed against one another by nonpositive engagement and nonpivotably.

In one embodiment of the invention, this is done by providing protrusions 60 or recesses on an outer side 58 of a fin 48; they cooperate with recesses 62 or protrusions on an inner face 64 of the legs 34 of the fork head in complementary fashion, generating a deflection of the spring tongue 52 in the axial direction and hence prestressing in the axial direction 30 inside the pressure piece 16. By means of this axial prestressing, the pressure piece 16 then presses with its sliding face 46 against the ball head 26 and presses the ball head in turn against the spherical cap 28 of the fork head 14, so that these components are placed nondisplaceabiy relative to one another.

Such a protrusion in the radial direction along the outer side 58 of the fin 48 of the pressure piece is not, however, absolutely required; in particular, it would be conceivable for the pressure piece, with its axial face end 66 to engage a graduation on the inside or inner face 64 of the leg 34 of the fork head 14 from beneath; this graduation then protrudes radially inward. For example, the pressure piece could then be rotated into this contact position by rotation about the axial direction 30, In other words, the pressure piece 16, in a first rotary position, is inserted axially into the fork head 14 and then rotated about the axial direction 30, so that the spring tongue 52 comes into contact axially with a protrusion or a graduation in the applicable leg 34 of the fork head and as a result is deflected axially, so that the axial prestressing in the pressure piece 16 is built up.

In the exemplary embodiment shown in FIGS. 1 through 3, both legs 34 of the fork head 14, as an example, include a groovelike recess 62, which for example extends horizontally, and which is engaged by the respective spring tongue 52; the spring tongue 52 protrudes radially past the outer side 58 of the respective fin 48. However, it is also conceivable and advantageous that the pressure piece 16 is first introduced in the axial direction 30 into the fork head 14 in a first rotary position, in which the fins are oriented in the vicinity of the groove 32 between the legs 34 of the fork head 14, and then is screwed in about the axial direction 30 into the intended installed position shown in the drawings. Then, there is not the risk that the spring tongues will be excessively deflected in the other direction before being latched or clipped into place.

FIGS. 2a and 2b show different embodiments of the groovelike recess 62, both of them suitable for the pressure piece 16 shown in FIG. 3a. In FIG. 2a, the groovelike recess 62 extends over the entire circumferential extent of the respective leg 34, and in FIG. 2b it extends only partway around.

Figure 2D:
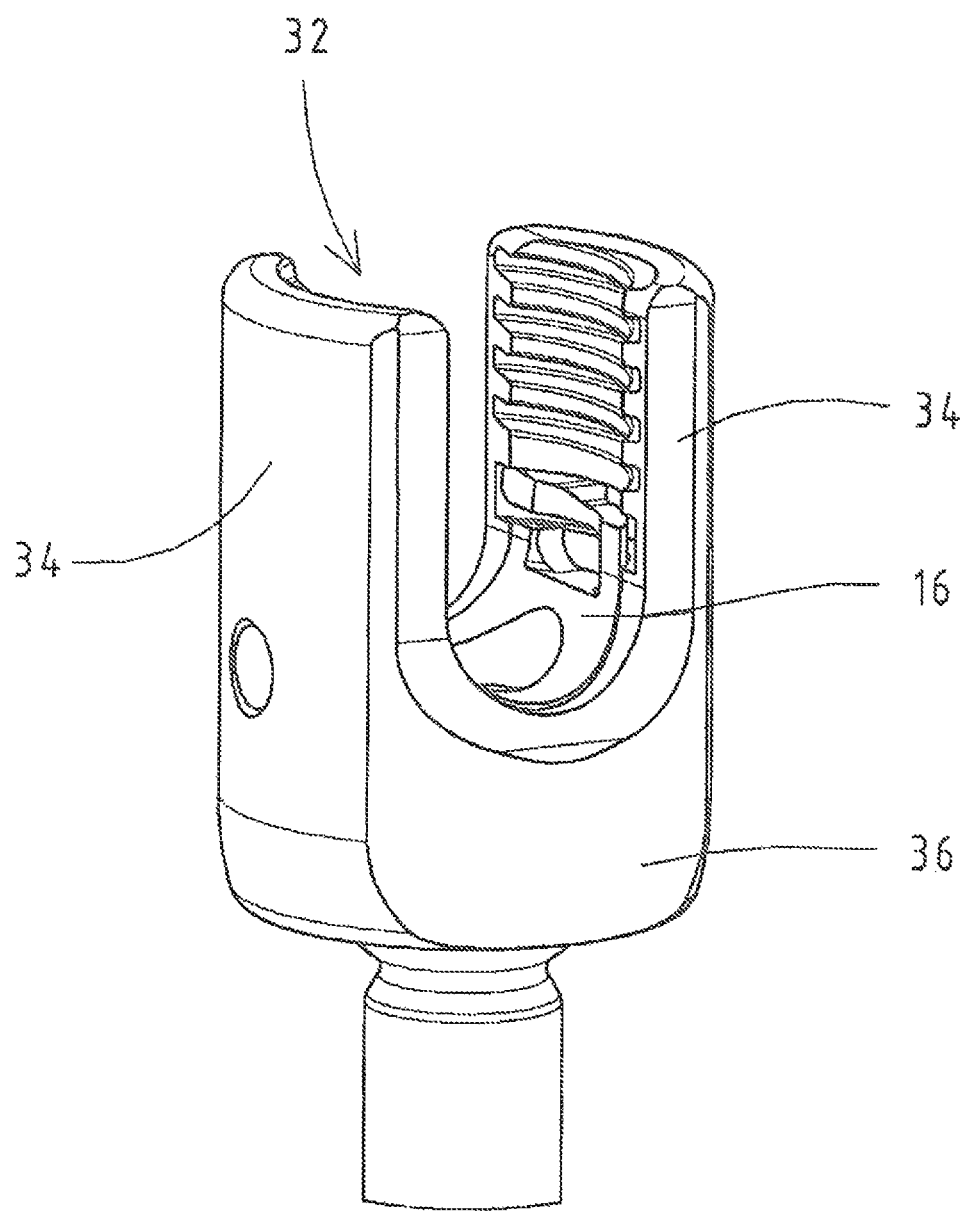

FIGS. 2c and 2d show the osteosynthesis device of the invention with a pressure piece 16 of FIG. 3a inserted into the fork head.

Finally, FIGS. 3b and 3c show further embodiments of the pressure piece 16, which differ from the rotationally symmetrical embodiment of the pressure piece shown in FIG. 3a. In FIG. 3b, the spring tongues 52 are embodied mirror-symmetrically with respect to a plane that includes the axial direction 30 and are located on the pressure piece 16. In the embodiment of FIG. 3c, a spring tongue 52 is embodied on only one fin 48. In the case of the opposite fin 48, however, a radial projection beyond the outer side 58 of this fin 48 is embodied on its free end, which forms a protrusion 60 and can engage a groovelike recess 62 in the associated leg 34 of the fork head. It has been demonstrated that even in a one-sided embodiment of a spring tongue 52, sufficient axial prestressing in the pressure piece 16 to place the fork head 14 nonpivotably relative to the ball head 26 of the bone screw 12 is achievable, so that when the bone screw 12 is being screwed into the bone, the fork head 14 can be held in a suitable position.

Further, in a first variant of the invention, it is provided that in all the pressure pieces 16 of FIGS. 3a-c, a protrusion 70 is provided, which protrudes into the slit 60 in the axial direction and thus serves as a stop 72 for limiting a deflection of the spring tongue 52. Thus the respective spring tongue 52 can be deflected axially only are enough that it axially contacts this protrusion 70 or stop 72. In the embodiments shown as examples, this protrusion 70 is integrally formed onto the fixed part of the respective fin 48 of the pressure piece 16, However, it would also be possible for the protrusion to be integrally formed onto the movable spring tongue 52. This protrusion 70 and the resultant limitation in the deformation or deflection of the respective spring tongue 52 brought about according to the invention proves to be especially advantageous. Specifically, if during manipulation while the osteosynthesis device is being implanted, in particular when the bone screw 12 is being screwed in, pressure is exerted from above on the fork head 14, then the ball head 26 presses from below against the pressure piece 16 and, if the deflection of the spring tongues 52 were not limited, it would push the pressure piece 16 axially upward and thus bring about the danger of plastic deformation of the spring tongues 52. However, that cannot occur, or can occur to only a lesser extent, because of the protrusion 70 which is provided according to the invention and forms a stop 72 for the deflection of the spring tongue 52.

FIGS. 4a-c show an embodiment of the osteosynthesis device in a second variant of the invention. As in the case of the pressure pieces of FIGS. 3a-c, a spring tongue 52 is formed in that a slit 50 is formed in the applicable fin 48. However, in these embodiments of FIGS. 4a-c, a limitation of the deflection of the spring tongues 52 is not formed by a protrusion protruding into the slit 50, but instead, as seen in FIGS. 4b and c, the spring tongue 52 itself, in the vicinity of its end 56 joined to the fin 48, forms a stop 74 for limiting further deflection of the spring tongue 52. This is implemented according to the invention in that the spring tongue 52, in the state in which it is installed on the fork head 14 and seated on the ball head but is not additionally axially stressed, is spaced apart, in the vicinity of its end 56 joined to the fin 48, in the axial direction 30 from the fork head 14, or in other words does not rest against an axial support face 76, protrusion, recess, or other arbitrary axial contact face on the fork head 14. Nevertheless, in this state the pressure piece 16 is held with prestressing on the fork head 14, because the spring tongue 52, for example in the vicinity of its free end 54, is braced against the fork head 14 and specifically against the axial support face 76 of the fork head. If now—as indicated in FIG. 4c—an additional axially acting force is exerted between the ball head and the fork head, then the spring tongue 52 is deflected further, until the stop 74, in the vicinity of the end 56 of the spring tongue 52 joined to the fin 48, strikes the axial support face 76 of the fork head and limits any more-extensive deformation. In this embodiment according to the second variant of the invention, a protrusion protruding into the slit 50 is not necessary; however, it could additionally be provided. In a corresponding way, in a pressure piece of the first variant of the invention, the end of the spring tongue-joined to the fin could additionally function as a stop relative to the fork head.

The invention claimed is:

1. An osteosynthesis device, comprising:
a bone screw (12) which has a threaded shaft (24) and a ball head (26), and having a fork head (14) which has a groove (32) and two legs (34) for receiving a connection rod (18), the ball head (26) being pivotably supported in the fork head (14), and having one single pressure piece (16) which is seated on the ball head (26), the pressure piece (16) being braced on the fork head (14) and having two lateral fins (48) extending in an axial direction (30) of the fork head (14) and away from the threaded shaft (24), the one single pressure piece being constructed and arranged to be directly contacted by the connection rod (18), wherein the pressure piece (16) is supported in the fork head (14), with prestressing in the axial direction (30) and thus the direction toward the ball head (26) and wherein at least one of the fins (48) is slit transversely to the axial direction (30) of the fork head (14), so that a slit (50) extending in a circumferential direction and extending radially through the fin (48) is formed which slit (50) forms a spring tongue (52), and the pressure piece (16) is thereby resiliently embodied and is braced via the spring tongue(52) on the fork head (14);
and wherein a protrusion (70) embodied in one piece with the pressure piece (16) protrudes in the axial direction (30) into the slit (50); and wherein the protrusion (70), for limiting deformation or deflection of the spring tongue (52), forms a stop (72), acting in the axial direction (30), for the spring tongue (52).

2. The osteosynthesis device of claim 1, characterized in that the protrusion (70) is embodied opposite, in the axial direction (30), the spring tongue (52) on the pressure piece (16).

3. The osteosynthesis device of claim 1, characterized in that the protrusion (70) is embodied on the spring tongue (52).

4. The osteosynthesis device of claim 1, characterized in that the protrusion (70) is embodied on a free end (54) of the spring tongue (52) or on a region of the pressure piece opposite the free end of the spring tongue in the axial direction.

5. The osteosynthesis device of claim 1, characterized in that the pressure piece (16) and its fins (48) are embodied axially symmetrically, to the axial direction (30) of the fork head (14).

6. The osteosynthesis device of claim 1, characterized in that the pressure piece (16) and its fins (48) are embodied mirror-symmetrically to a plane that includes the axial direction (30) of the fork head.

7. The osteosynthesis device of claim 1, characterized in that the slit (50) is embodied in rounded fashion on a closed end (56) of the spring tongue (52).

8. The osteosynthesis device of claim 1, characterized in that the deflection of the spring tongue (52), upon a clasping or latching or screwing in of the pressure piece into an installed position in the fork head (14), amounts to at most 1.0 mm.

9. The osteosynthesis device of claim 1, characterized in that on outer sides of the fins (48) of the pressure piece (16), there are protrusions (60) or recesses, which cooperate in intermeshing fashion with recesses (62) or protrusions on inside surfaces of the legs (34) of the fork head (14).

10. The osteosynthesis device of claim 1, characterized in that the pressure piece (16) engages a graduation, located on an inner side of a leg (34) of the fork head (14), from beneath or engages the inside of a recess embodied there.

11. The osteosynthesis device of claim 1, characterized in that one fin (48) or both fins of the pressure piece (16) are embodied with multiple slits, which are cut inward into the fin or fins (48) in alternation from one side and a side opposite that side transversely to the axial direction (30) of the fork head (14).

12. The osteosynthesis device of claim 1, characterized in that the pressure piece (16) directly or indirectly forms a support for a connecting rod (18).

13. The osteosynthesis device of claim 1, characterized in that the pressure piece (16) is secured against relative rotation with respect to the fork head (14).

14. The osteosynthesis device of claim 1, characterized in that the spring tongue (52) is embodied as thicker on a free end (54) in the radial and/or axial direction than at a closed end (56).

15. An osteosynthesis device comprising a bone screw (12) which has a threaded shaft (24) and a ball head (26), and having a fork head (14) which has a groove (32) and two legs (34) for receiving a connection rod (18), the ball head (26) being pivotably supported in the fork head (14), and having one single pressure piece (16) which is seated on the ball head (26), the pressure piece (16) being braced on the fork head (14) and having two lateral fins (48) extending in an axial direction (30) of the fork head (14) and away from the threaded shaft (24), the one single pressure piece being constructed and arranged to be directly contacted by the connection rod (18), wherein the pressure piece (16) is supported in the fork head (14) with prestressing in the axial direction (30) and thus the direction toward the ball head (26) and wherein at least one of the fins (48) is slit transversely to the axial direction (30) of the fork head (14), so that a slit (50) extending in a circumferential direction and extending radially through the fin (48) is formed which slit (50) forms a spring tongue (52) on the fork head (14); and that the spring tongue (52), in a state in which it is installed on the fork head but is not in an additionally axially stressed state, is spaced apart at a closed end (56), is joined to the fin (48), from the fork head (14) in the axial direction (30); and wherein the spring tongue (52), in the additionally axially stressed state, in the vicinity of its end (56) joined to the fin (48) forms a stop (74) and can be braced with the stop (74) against the fork head (14) for limiting more-extensive deformation or deflection of the spring tongue (52).

16. The osteosynthesis device of claim 15, characterized in that the deflection of the spring tongue (52), upon a clasping or latching or screwing in of the pressure piece into an installed position in the fork head (14), amounts to at most 1.0 mm.

17. An osteosynthesis device, comprising:
a bone screw (12) which has a threaded shaft (24) and a ball head (26), and having a fork head (14) which has a groove (32) and two legs (34) for receiving a connection rod (18), the ball head (26) being pivotably supported in the fork head (14), and having one single pressure piece (16) which is seated on the ball head (26), the pressure piece (16) being braced on the fork head (14) and having two lateral fins (48) extending in an axial direction (30) of the fork head (14) and away from the threaded shaft (24), the one single pressure piece being constructed and arranged to be directly contacted by the connection rod (18), wherein the pressure piece (16) is supported in the fork head (14), with prestressing in the axial direction (30) and thus the direction toward the ball head (26) and wherein at least one of the fins (48) is slit transversely to the axial direction (30) of the fork head (14), so that a slit (50) extending in a circumferential direction and extending radially through the fin (48) is formed which slit (50) forms a spring tongue (52), and the pressure piece (16) is thereby resiliently embodied and is braced via the spring tongue (52) on the fork head (14);
and wherein a protrusion (70) embodied in one piece with the pressure piece (16) protrudes in the axial direction (30) into the slit (50) and is embodied opposite the spring tongue (52) on the pressure piece (16); and that the protrusion (70), and wherein the protrusion (70) for limiting deformation or deflection of the spring tongue (52), forms a stop (72), acting in the axial direction (30), for the spring tongue (52) and that the deflection of the spring tongue (52), upon a clasping or latching or screwing in of the pressure piece into an installed position in the fork head (14), amounts to at most 1.0 mm.

* * * * *